United States Patent
Liu et al.

(10) Patent No.: US 11,860,266 B2
(45) Date of Patent: Jan. 2, 2024

(54) DETECTION SYSTEM AND METHOD OF DETECTING LIFE USING RADAR

(71) Applicant: RichWave Technology Corp., Taipei (TW)

(72) Inventors: Keng-Hao Liu, Taipei (TW); Han-Jieh Chang, Taipei (TW); Hsiang-Feng Chi, Taipei (TW)

(73) Assignee: RichWave Technology Corp., Taipei (TW)

( * ) Notice: Subject to any disclaimer, the term of this patent is extended or adjusted under 35 U.S.C. 154(b) by 384 days.

(21) Appl. No.: 17/169,568

(22) Filed: Feb. 8, 2021

(65) Prior Publication Data

US 2021/0255302 A1   Aug. 19, 2021

(30) Foreign Application Priority Data

Feb. 14, 2020   (TW) .................................. 109104633

(51) Int. Cl.
| | |
|---|---|
| *G01S 13/56* | (2006.01) |
| *A61B 5/0507* | (2021.01) |
| *A61B 8/08* | (2006.01) |
| *G01S 13/58* | (2006.01) |

(52) U.S. Cl.
CPC ............ *G01S 13/56* (2013.01); *A61B 5/0507* (2013.01); *A61B 8/488* (2013.01); *G01S 13/58* (2013.01)

(58) Field of Classification Search
CPC ................................. G01S 13/56; G01S 13/58
USPC ........................................ 342/28, 21, 71, 442
See application file for complete search history.

(56) References Cited

U.S. PATENT DOCUMENTS

| | | | |
|---|---|---|---|
| 2010/0027378 A1 | 2/2010 | Sabatier | |
| 2015/0160335 A1* | 6/2015 | Lynch | ................. G01S 13/4418 |
| | | | 342/194 |
| 2016/0089113 A1* | 3/2016 | Choi | ..................... G01S 15/892 |
| | | | 600/438 |
| 2017/0254895 A1* | 9/2017 | Tong | ..................... G01S 13/867 |

(Continued)

FOREIGN PATENT DOCUMENTS

| | | |
|---|---|---|
| CN | 109425856 A | 3/2019 |
| CN | 110579758 A | 12/2019 |
| TW | 201336478 A | 9/2013 |

(Continued)

*Primary Examiner* — Bo Fan
(74) *Attorney, Agent, or Firm* — Winston Hsu

(57) ABSTRACT

A method of detecting a life includes receiving an echo signal including an in-phase component and a quadrature component, performing a preprocessing procedure on the echo signal to generate a preprocessed signal, generating, according to the preprocessed signal, complex conjugate data associated with the in-phase component and the quadrature component, performing a first time-domain-to-frequency-domain transform on the complex conjugate data to generate Doppler spectrogram data comprising a plurality of positive velocity energies and a plurality of negative velocity energies, generating combined Doppler spectrogram data according to the plurality of positive velocity energies and the plurality of negative velocity energies, performing a second time time-domain-to-frequency-domain transform on the combined Doppler spectrogram data to generate spectrum data, and determining whether a life is detected according to the spectrum data.

20 Claims, 6 Drawing Sheets

(56) References Cited

U.S. PATENT DOCUMENTS

2019/0353752 A1* 11/2019 Lin .................... A61B 5/05

FOREIGN PATENT DOCUMENTS

| TW | 201546474 A | 12/2015 |
| TW | I660187 B | 5/2019 |
| TW | 202004774 A | 1/2020 |

* cited by examiner

DETECTION SYSTEM AND METHOD OF DETECTING LIFE USING RADAR

CROSS REFERENCE TO RELATED APPLICATION

This non-provisional application claims priority of Taiwan patent application No. 109104633, filed on 14 Feb. 2020, included herein by reference in its entirety.

TECHNICAL FIELD

The invention relates to target detection, and in particular, to a detection system and a method of detecting a life.

BACKGROUND

Biometrics is an important technology for identifying humans, animals and other life, and has been widely used in the field of intrusion detection. Radar has been used in biometric technology owing to its performance being unaffected in night environments, harsh environments and poor lighting environments. However, in practice, using radar to achieve accurate and quick detection of life remains difficult.

SUMMARY

According to an embodiment of the invention, a method of detecting a life includes receiving an echo signal comprising an in-phase component and a quadrature component, performing a preprocessing procedure on the echo signal to generate a preprocessed signal, generating, according to the preprocessed signal, complex conjugate data associated with the in-phase component and the quadrature component, performing a first time-domain-to-frequency-domain transform on the complex conjugate data to generate Doppler spectrogram data comprising a plurality of positive velocity energies and a plurality of negative velocity energies, generating combined Doppler spectrogram data according to the plurality of positive velocity energies and the plurality of negative velocity energies, performing a second time time-domain-to-frequency-domain transform on the combined Doppler spectrogram data to generate spectrum data, and determining whether a life is detected according to the spectrum data.

According to an embodiment of the invention, a detection system for use to detect a life includes a receiver, a preprocessing circuit and a processor. The receiver is used to receive an echo signal comprising an in-phase component and a quadrature component, the echo signal being generated by a life. The preprocessing circuit is coupled to the receiver, and used to perform a preprocessing procedure on the echo signal to generate a preprocessed signal. The processor is coupled to the preprocessing circuit, and used to generate, according to the preprocessed signal, complex conjugate data associated with the in-phase component and the quadrature component, perform a first time-domain-to-frequency-domain transform on the complex conjugate data to generate Doppler spectrogram data comprising a plurality of positive velocity energies and a plurality of negative velocity energies, generate combined Doppler spectrogram data according to the plurality of positive velocity energies and the plurality of negative velocity energies, perform a second time time-domain-to-frequency-domain transform on the combined Doppler spectrogram data to generate spectrum data, and determine whether the life is detected according to the spectrum data.

DETAILED DESCRIPTION

Figure 1:
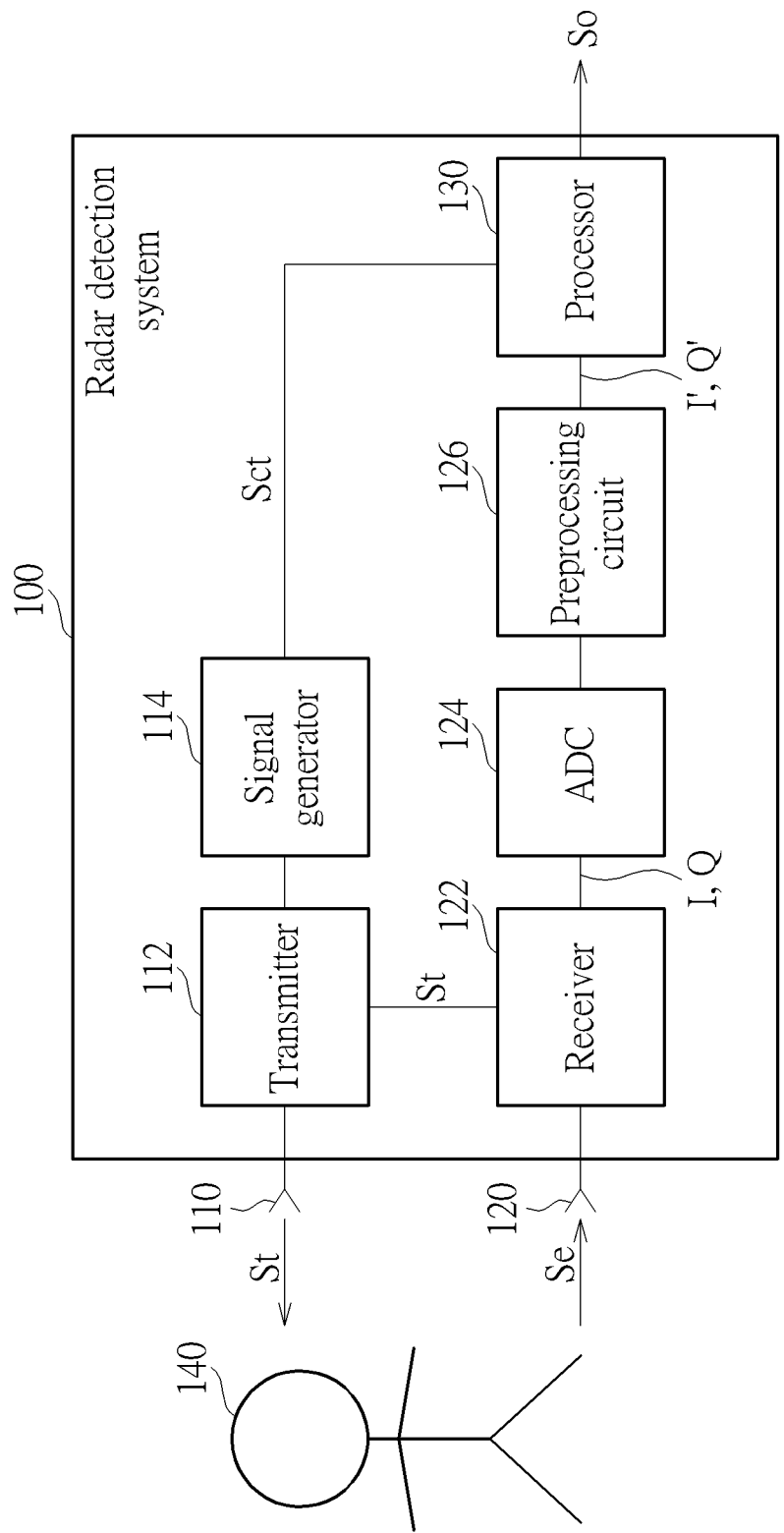
FIG. 1 is a block diagram of a radar detection system according to an embodiment of the invention.

FIG. 1 is a block diagram of a radar detection system 100 according to an embodiment of the invention. The radar detection system 100 may detect a sign of a life, and may be a frequency-modulated continuous wave (FMCW) radar. The life may be a human being, a pet or others. The sign of life may be breath, heartbeats or others. Since breaths or heartbeats results from expansion and contraction of a heart, a chest or other body parts at a predetermined frequency, the radar detection system 100 may determine a movement feature of the a target object 140, so as to determine whether the movement feature matches a pattern of the sign of life, thereby determining whether the target object 140 is a life. The radar detection system 100 may transmit a transmission signal St and receive an echo signal Se reflected from the target object 140, and determine whether the target object 140 is a life according to the echo signal Se. The radar detection system 100 may include antennas 110, 120, a transmitter 112, a signal generator 114, a receiver 122, an analog-to-digital converter (ADC) 124, a preprocessing circuit 126 and a processor 130. The antenna 110, the transmitter 112, the signal generator 114 and the processor 130 may be sequentially coupled to each other. The antenna 120, the receiver 122, the ADC 124, the preprocessing circuit 126 and the processor 130 may be sequentially coupled to each other.

The processor 130 may generate a baseband signal for a frequency-modulated continuous wave signal by controlling the signal generator 114 via a control signal Sct. The transmitter 112 may convert the frequency-modulated continuous wave signal into a transmission signal St to a predetermined frequency band (e.g., 6 GHz), and then the antenna 110 may transmit the transmission signal St. The frequency-modulated continuous wave may be a triangular wave, a saw-toothed wave, a staircase wave, a sinusoidal wave or other shapes of waves. The receiver 122 may receive the echo signal Se via the antenna 120, and mix the echo signal Se and a signal associated with the transmission signal St, e.g., the transmission signal St to generate a beat signal. The beat signal carries beat information indicative of a half of a difference between the frequency of the echo signal Se and the frequency of the transmission signal St. The echo signal Se may include an in-phase component and a quadrature component at each point in time, and the beat signal may include a corresponding in-phase component I and a corresponding quadrature component Q at each point in time. The receiver 122 may mix the beat signal with two orthogonal oscillating signals to obtain the in-phase component I and the quadrature component Q of the beat signal. The ADC 124 may set a predetermined sampling frequency, e.g., 44 kHz to be the sampling frequency, and sample the in-phase component I and the quadrature component Q of the beat signal to generate a digitized in-phase component and a digitized quadrature component. The preprocessing circuit 126 may perform a preprocessing procedure on the digitized in-phase component and the digitized quadrature component to generate preprocessed in-phase component I' and preprocessed quadrature component Q'. The preprocessing procedure may include filtering out a high frequency noise, reducing a sampling frequency, removing a direct current component, and a combination thereof. The preprocessing circuit 126 may include a low-pass filter, a decimator, an average circuit, an adder and a combination thereof. The low-pass filter may remove high frequency components from the digitized in-phase component and the digitized quadrature component to generate filtered in-phase component and filtered quadrature component. The decimator may reduce the quantity of data, e.g., reduce the filtered in-phase components and the filtered quadrature components at 44$k$ samples per second by a factor of 80 to generate downsampled in-phase components and quadrature components at 550 samples per second. The downsampled data may reduce computations of subsequent signal processing, preventing signal distortion and false detection of a life owing to the filter being unable to process a large quantity of data in the subsequent filtering process. The direct current components in the downsampled in-phase components and the downsampled quadrature components may be obtained by averaging the downsampled in-phase components and the downsampled quadrature components over a period of time, respectively. The average circuit may compute the averages of the downsampled in-phase components and downsampled quadrature components, e.g., compute 128-data moving averages to generate the average of the downsampled in-phase components and downsampled quadrature components. The adder may remove the average of the downsampled in-phase components from the downsampled in-phase component to generate the preprocessed in-phase component I', remove the average of the downsampled quadrature components from the downsampled quadrature component to generate the preprocessed quadrature component Q', thereby simplifying the subsequence complex signal demodulation process and preventing the subsequence complex signal demodulation process from being affected by the direct current offset. In some embodiments, the preprocessing procedure may be implemented by software or a combination of software and hardware. In the software implementation, the processor 130 may store the software in a memory of the radar detection system 100 and load the software from the memory to execute the preprocessing process.

Figure 2:
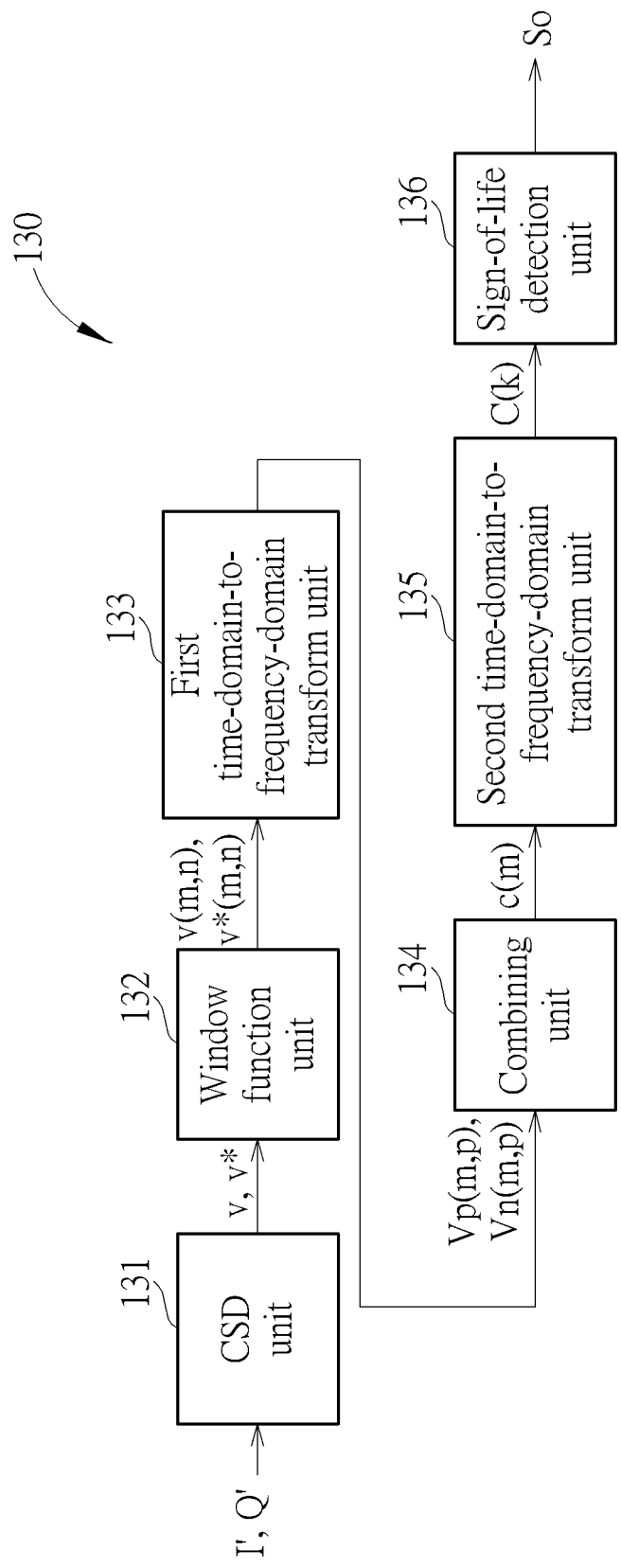
FIG. 2 is a block diagram of the processor in FIG. 1.

The processor 130 may detect the sign of life according to the preprocessed in-phase component I' and the preprocessed quadrature component Q', and generate an output signal So to indicate whether a life is detected. FIG. 2 is a block diagram of the processor 130. The processor 130 may include complex signal demodulation (CSD) unit 131, a window function unit 132, a first time-domain-to-frequency-domain transform unit 133, a combining unit 134, a second time-domain-to-frequency-domain transform unit 135 and a sign-of-life detection unit 136, the units being sequentially coupled to each other. Each of the units may be implemented by software, hardware or a combination thereof.

The complex signal demodulation unit 131 may construct complex conjugate data v, v* according to the in-phase component I' and the quadrature component Q', e.g., v=I'+Q', v*=I'−Q'. In some embodiments, v=Q'±I', v*=Q'−I'.

The window function unit 132 may employ a window function to divide the complex conjugate data v, v* using a fixed period of time to generate M time intervals of complex conjugate data v, v*, each time interval of complex conjugate data v, v* including N pairs of complex conjugate data v(m,n), v*(m,n), m, n being positive integers, 1≤m≤M 1≤n≤N. The window function may have a fixed length, and may be a rectangular window function, a Hamming window function, a Hanning window function or other types of window functions. For example, the window function unit 132 may employ the window function to divide the complex data v at a fixed length of 64 pieces of data, the complex data v(2,32) representing the 32th piece of complex data in the second time interval.

Figure 3:
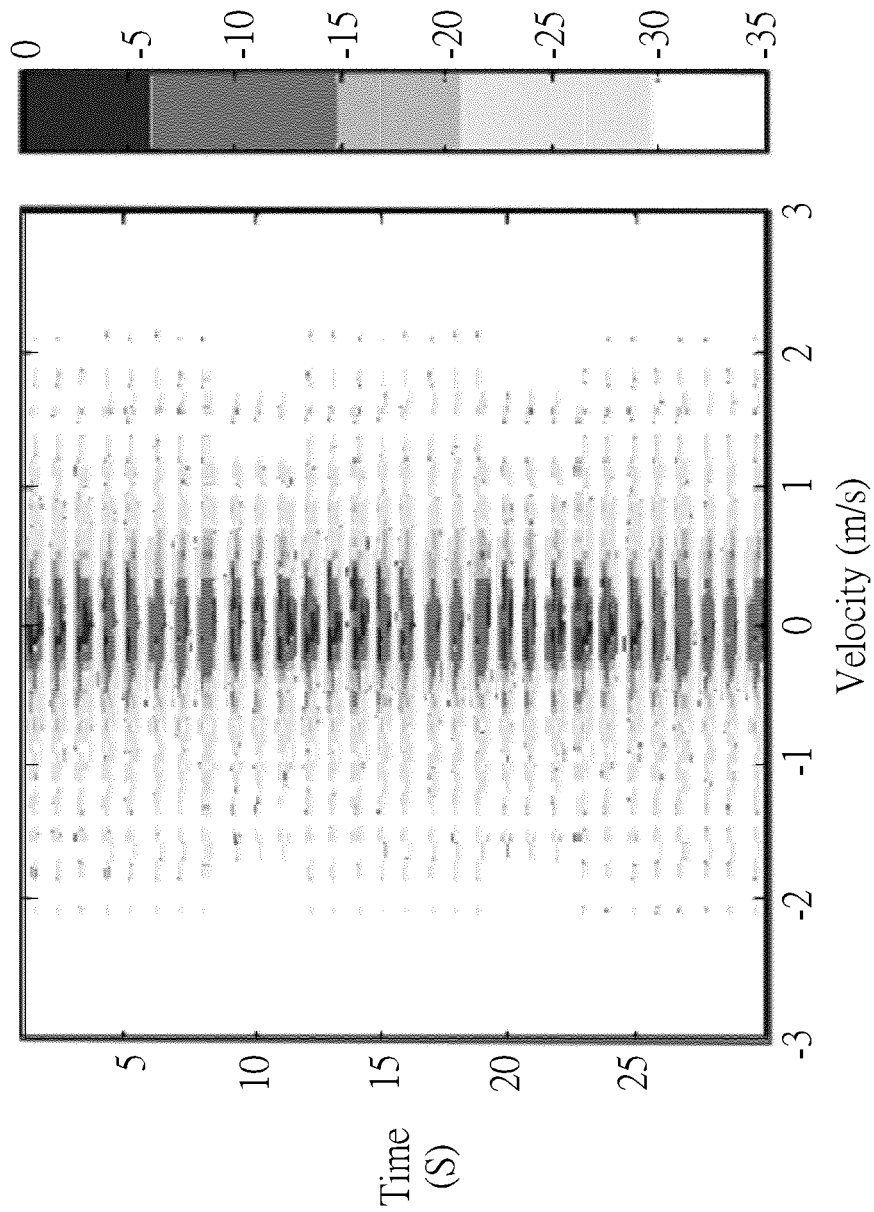
FIG. 3 is a schematic diagram of a Doppler spectrogram.

The first time-domain-to-frequency-domain transform unit 133 may perform a first time-domain-to-frequency-domain transform on the complex data v(m,n) to generate a positive velocity energy Vp(m,p) corresponding to the pth positive velocity in the mth time interval, p being a positive integer, 1≤p≤P, and a positive velocity energy Vp(2,32) representing the 32th positive velocity energy in the second time interval. Similarly, the first time-domain-to-frequency-domain transform unit 133 may perform the first time-domain-to-frequency-domain transform on the complex data v*(m,n) to generate a negative velocity energy Vn(m,p) corresponding to the pth negative velocity in the mth time interval. The positive velocity energy Vp(m,p) and the negative velocity energy Vn(m,p) may be the energies corresponding to a positive velocity (e.g., representing the target object 140 moves towards the radar detection system 100) and a negative velocity (e.g., representing the target object 140 moves away from the radar detection system 100) respectively. The first time-domain-to-frequency-domain transform may be implemented by a short-time Fourier transform, a wavelet transform, a Hilbert-Huang Transform, or a combination thereof. In some embodiments, P=N, the first time-domain-to-frequency-domain transform unit 133 may output positive velocity energies Vp(1,1) to Vp(M,N) and negative velocity energies Vn(1,1) to Vn(M,N) for subsequent use. The positive velocity energies Vp(1,1) to Vp(M,N) and the negative velocity energies Vn(1,1) to Vn(M,N) may be referred to as Doppler spectrogram data. The processor 130 may plot a Doppler spectrogram according to the Doppler spectrogram data, as shown in FIG. 3, in which the horizontal axis represents velocity, and the vertical axis represents time, and the colors represent energies corresponding to the velocities. The Doppler spectrogram shows that the velocity of the target object 140 oscillates substantially between +1 m/s and −1 m/s.

The combining unit 134 may perform a combination operation according to the positive velocity energies Vp(m, p) and the negative velocity energies Vn(m,p) to generate combined Doppler spectrogram data c(m). In some embodiments, the combining unit 134 may perform a linear combination on the positive velocity energies Vp(m,1) to Vp(m, P) and the negative velocity energies Vn(m,1) to Vn(m,P) to generate the combined Doppler spectrogram data c(m). For example, the combining unit 134 may accumulate the positive velocity energies Vp(m,1) to Vp(m,P) and the negative velocity energies Vn(m,1) to Vn(m,P) to generate the combined Doppler spectrogram data c(m). In other embodiments, the combining unit 134 may generate the combined Doppler spectrogram data c(m) according to an extremum (e.g., an absolute value of a maximum energy) of the positive velocity energies Vp(m,1) to Vp(m,P) and the negative velocity energies Vn(m,1) to Vn(m,P) in the mth time interval. For example, the combining unit 134 may determine the maximum of the positive velocity energies $V_p(m,1)$ to $V_p(m,P)$ and the negative velocity energies $V_n(m,1)$ to $V_n(m,P)$ in the mth time interval, and set the maximum as the combined Doppler spectrogram data $c(m)$.

In some embodiments, the combining unit 134 may enhance the positive velocity energies $V_p(m,p)$ and the negative velocity energies $V_n(m,p)$ to generate enhanced positive velocity energies and enhanced negative velocity energies, and generate the combined Doppler spectrogram data $c(m)$ according to the enhanced positive velocity energies and enhanced negative velocity energies. For example, the combining unit 134 may apply a non-linear function, e.g., a logarithmic function by a filter or other signal processing methods to the positive velocity energies $V_p(m,p)$ and the negative velocity energies $V_n(m,p)$ to generate the enhanced positive velocity energies $\log(V_p(m,p))$ and enhanced negative velocity energies $\log(V_n(m,p))$. In some embodiments, the combining unit 134 may perform a linear combination on the enhanced positive velocity energies and the enhanced negative velocity energies to generate the combined Doppler spectrogram data $c(m)$. For example, the combining unit 134 may accumulate the enhanced positive velocity energies $\log(V_p(m,1))$ to $\log(V_p(m,P))$ and the enhanced negative velocity energies $\log(V_n(m,1))$ to $\log(V_n(m,P))$ to generate the combined Doppler spectrogram data $c(m)$. In other embodiments, the combining unit 134 may generate the combined Doppler spectrogram data $c(m)$ according to an extremum (e.g., an absolute value of a maximum energy) of the enhanced positive velocity energies $\log(V_p(m,1))$ to $\log(V_p(m,P))$ and the enhanced negative velocity energies $\log(V_n(m,1))$ to $\log(V_n(m,P))$ in the mth time interval. For example, the combining unit 134 may determine the maximum of the enhanced positive velocity energies $\log(V_p(m,1))$ to $\log(V_p(m,P))$ and the enhanced negative velocity energies $\log(V_n(m,1))$ to $\log(V_n(m,P))$ in the mth time interval, and set the maximum as the combined Doppler spectrogram data $c(m)$.

Figure 4:
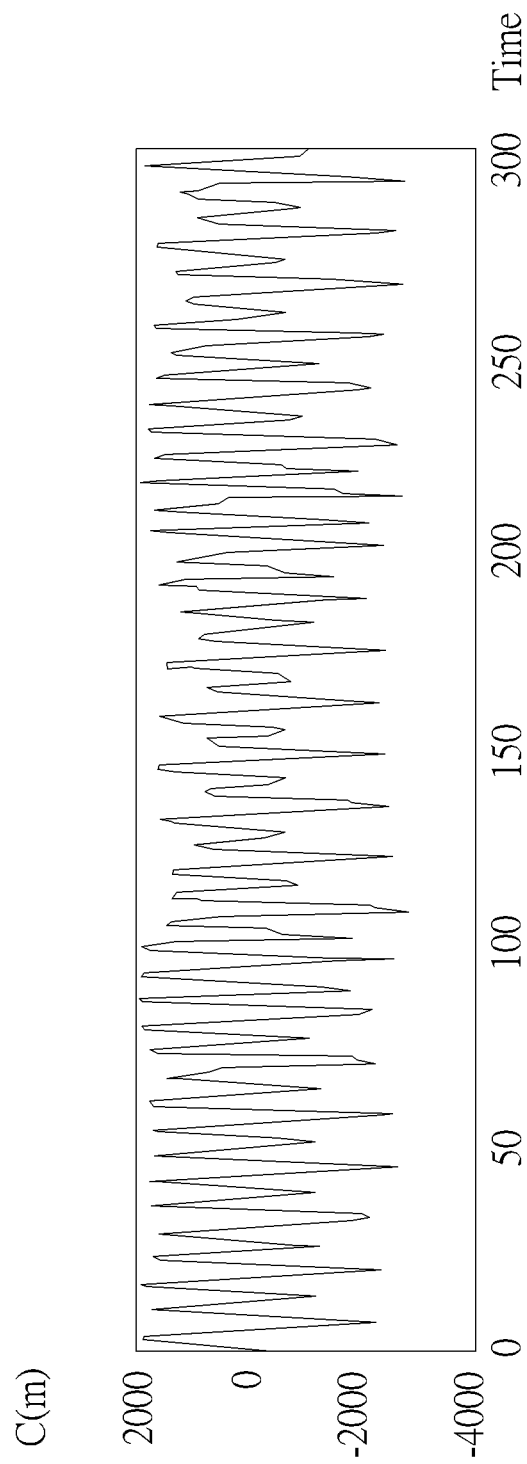
FIG. 4 is a schematic diagram of a combined Doppler spectrogram.

In some embodiments, the combining unit 134 may normalize the positive velocity energies $V_p(m,p)$ and the negative velocity energies $V_n(m,p)$ to generate normalized positive velocity energies and normalized negative velocity energies, and generate the combined Doppler spectrogram data $c(m)$ according to the normalized positive velocity energies and normalized negative velocity energies. For example, the combining unit 134 may distribute all the positive velocity energies $V_p(1,1)$ to $V_p(M,P)$ between a predetermined positive velocity energy range in a proportional manner to generate the normalized positive velocity energies $V_{p\_norm}(1,1)$ to $V_{p\_norm}(M,P)$, and distribute all the negative velocity energies $V_n(1,1)$ to $V_n(M,P)$ between a predetermined negative velocity energy range in a proportional manner to generate the normalized negative velocity energies $V_{n\_norm}(1,1)$ to $V_{n\_norm}(M,P)$. The positive velocity energies may range between 0 and a predetermined maximum, and the negative velocity energies may range between 0 and a predetermined minimum. In some embodiments, the combining unit 134 may perform a linear combination on the normalized positive velocity energies $V_{p\_norm}(m,1)$ to $V_{p\_norm}(m,P)$ and the normalized negative velocity energies $V_{n\_norm}(m,1)$ to $V_{n\_norm}(m,P)$ to generate the combined Doppler spectrogram data $c(m)$. For example, the combining unit 134 may accumulate the normalized positive velocity energies $V_{p\_norm}(m,1)$ to $V_{p\_norm}(m,P)$ and the normalized negative velocity energies $V_{n\_norm}(m,1)$ to $V_{n\_norm}(m,P)$ in the mth time interval to generate the combined Doppler spectrogram data $c(m)$. The processor 130 may generate data corresponding to the combined Doppler spectrogram according to the combined Doppler spectrogram data $c(1)$ to $c(M)$. The combined Doppler spectrogram may be plotted, as shown in FIG. 4, in which the horizontal axis represents time, and the vertical axis represents the combined Doppler spectrogram data $c(m)$. The combined Doppler spectrogram shows that the combined energy of the target object 140 oscillates substantially between the maximum of the positive velocity energy range and the minimum of the negative velocity energy range (that is, the maximum of the absolute values of the negative velocity energies).

In some embodiments, after the positive velocity energies $V_p(m,p)$ and the negative velocity energies $V_n(m,p)$ are enhanced and/or normalized, the combining unit 134 may filter the enhanced and/or normalized positive velocity energies and enhanced and/or normalized negative velocity energies using a bandpass filter to generate filtered positive velocity energies and negative velocity energies, and accumulate the filtered positive velocity energies and negative velocity energies in the mth time interval to generate the combined Doppler spectrogram data $c(m)$. The predetermined velocity range may be, for example, between +1 m/s and −1 m/s. In some embodiments, the combining unit 134 may filter out components in the combined Doppler spectrogram data $c(m)$ outside a predetermined frequency range using another bandpass filter or low-pass filter. The predetermined frequency range may be configured according to a normal heart rate or a normal respiratory rate, e.g., the normal heart rate of an adult ranges substantially between 60 and 100 beats per minute, and the normal respiratory rate of an adult ranges substantially between 12 and 20 breaths per minute.

Figure 5:
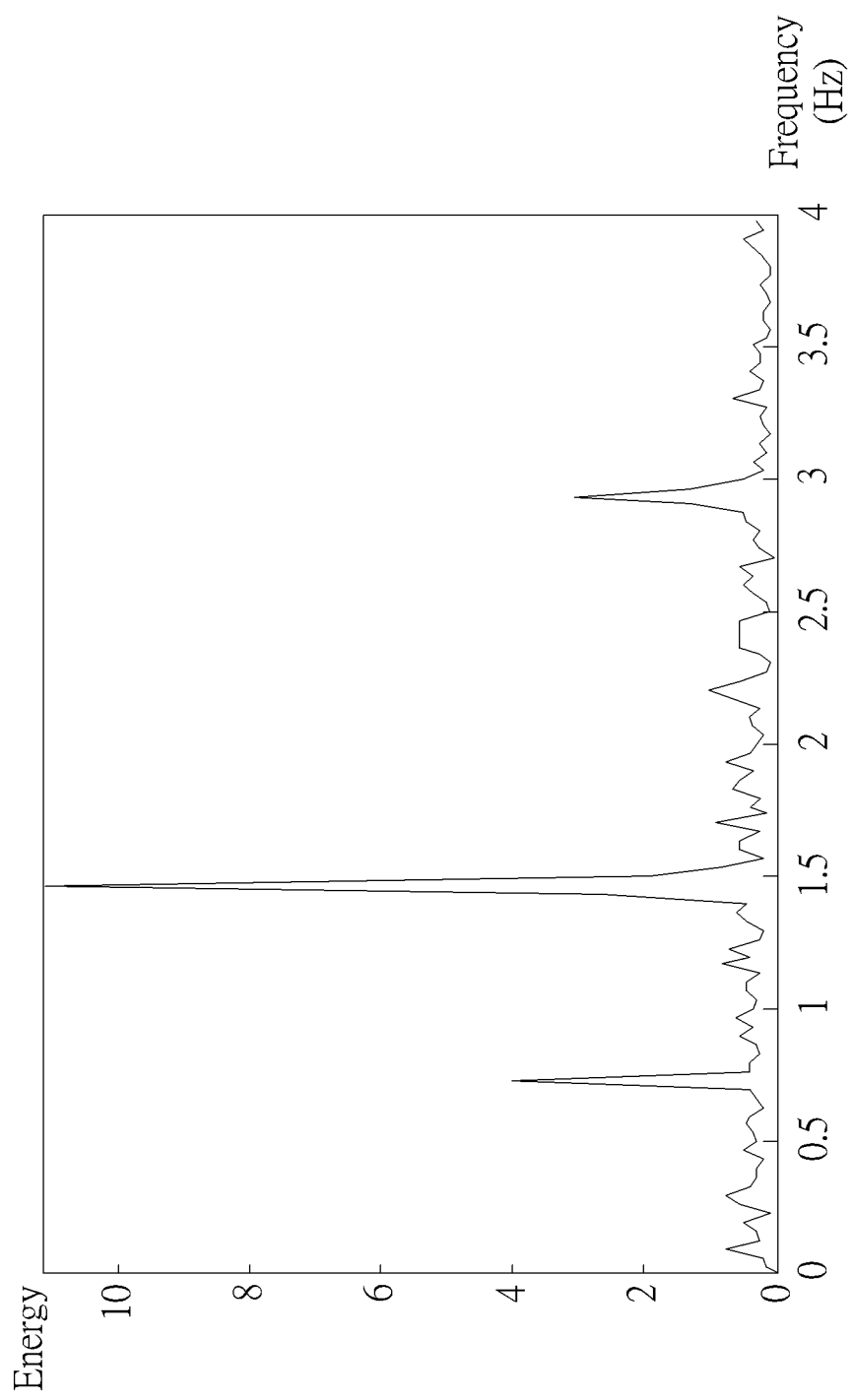
FIG. 5 is a schematic diagram of a spectrum.

The second time-domain-to-frequency-domain transform unit 135 may perform a second time-domain-to-frequency-domain transform on the combined Doppler spectrogram data $c(m)$ to generate spectrum data $C(k)$, k being a positive integer, $1 \leq k \leq K$. The spectrum data $C(k)$ represents an energy at a kth frequency band, e.g., spectrum data $C(2)$ represents the energy at the second frequency band. The second time-domain-to-frequency-domain transform may be implemented by a discrete Fourier transform or a fast Fourier transform. In some embodiments, K=M, the second time-domain-to-frequency-domain transform unit 135 may output spectrum data $C(1)$ to $C(M)$. The processor 130 may plot a spectrum diagram according to the spectrum data $C(1)$ to $C(M)$, as shown in FIG. 5, the horizontal axis representing frequency, and the vertical axis represent energy. The spectrum diagram shows that the spectrum data $C(1)$ to $C(M)$ of the target object 140 peak at 0.75 Hz, 1.5 Hz and 3 Hz.

The sign-of-life detection unit 136 may determine whether a life is detected according to the spectrum data $C(1)$ to $C(M)$. When a local maximum of the spectrum data $C(1)$ to $C(M)$ is within a sign-of-life range, the sign-of-life detection unit 136 may determine that a life is detected. When all local maxima of the spectrum data $C(1)$ to $C(M)$ are outside the sign-of-life range, the sign-of-life detection unit 136 may determine that the life is not detected. The sign-of-life range may be configured according to the normal heart rate, e.g., between 1 Hz and 2 Hz. The sign-of-life range may be configured according to the normal respiratory rate, e.g., between 0.2 Hz and 0.4 Hz. The sign-of-life detection unit 136 may output a detection result of the life as an output signal So to an output device of the radar detection system 100 such as a monitor, a printer or a speaker, or to a data storage device such as a hard drive.

The radar detection system 100 may generate complex conjugate data according to in-phase components and quadrature components of an echo signal to generate positive velocity energies and negative velocity energies of a target object and detect expansion and contraction movements of a living object, thereby determining whether the target object is a life in an accurate and quick manner.

Figure 6:
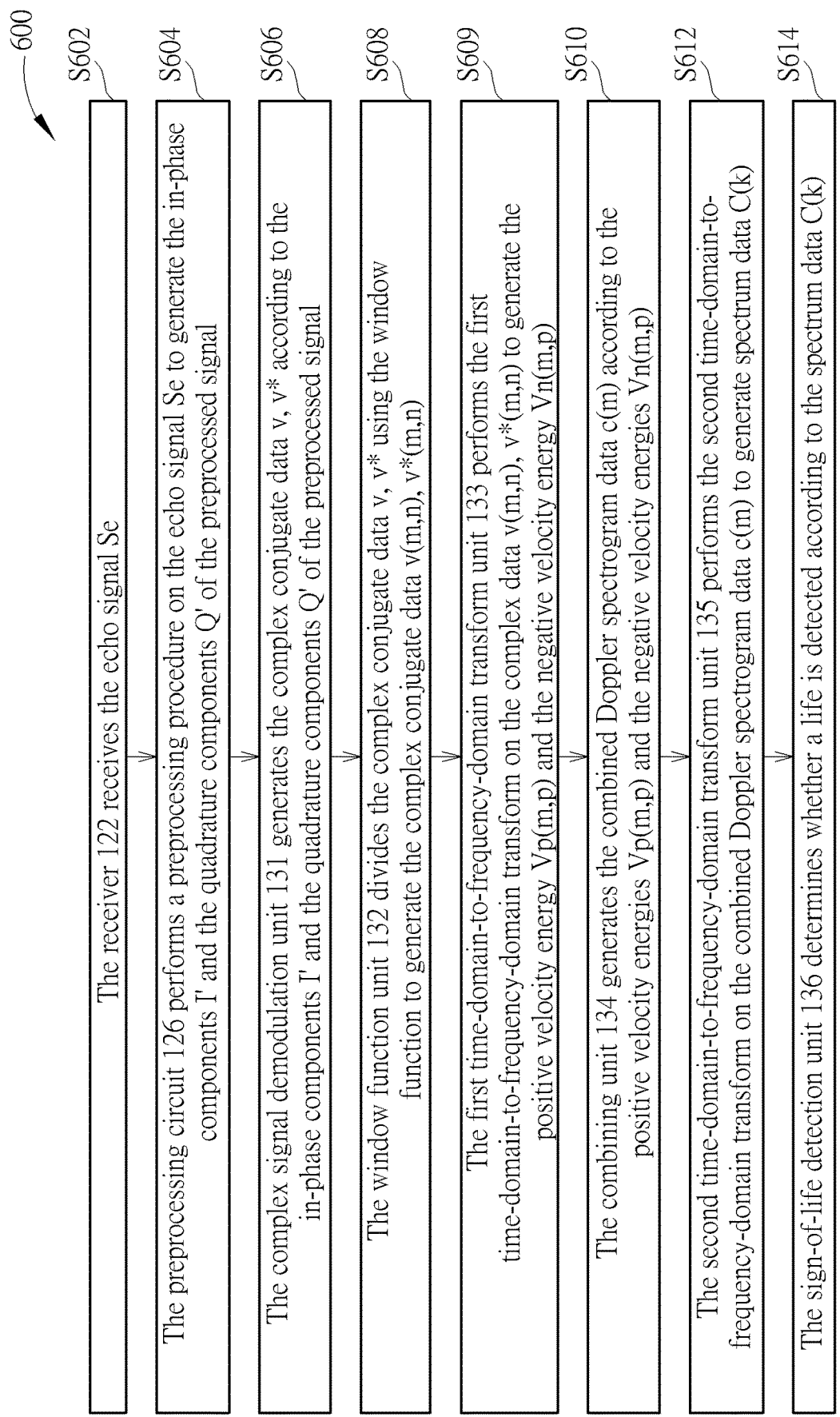
FIG. 6 is a flowchart of a method of detecting a life according to an embodiment of the invention.

FIG. 6 is a flowchart of a method 600 of detecting a life according to an embodiment of the invention. The method 600 may be adopted by the radar detection system 100, and may include Steps S602 to S614. Steps S602 to S609 are used to generate Doppler spectrogram data. Steps S610 to S614 are used to determine whether a life is detected according to the Doppler spectrogram data. Any reasonable step change or adjustment is within the scope of the disclosure. Steps S602 to S614 are explained using the radar detection system 100:

Step S602: The receiver 122 receives the echo signal Se;

Step S604: The preprocessing circuit 126 performs a preprocessing procedure on the echo signal Se to generate the in-phase components I' and the quadrature components Q' of the preprocessed signal;

Step S606: The complex signal demodulation unit 131 generates the complex conjugate data v, v* according to the in-phase components I' and the quadrature components Q' of the preprocessed signal;

Step S608: The window function unit 132 divides the complex conjugate data v, v* using the window function to generate the complex conjugate data v(m,n), v*(m,n);

Step S609: The first time-domain-to-frequency-domain transform unit 133 performs the first time-domain-to-frequency-domain transform on the complex data v(m,n), v*(m,n) to generate the positive velocity energy Vp(m,p) and the negative velocity energy Vn(m,p);

Step S610: The combining unit 134 generates the combined Doppler spectrogram data c(m) according to the positive velocity energies Vp(m,p) and the negative velocity energies Vn(m,p);

Step S612: The second time-domain-to-frequency-domain transform unit 135 performs the second time-domain-to-frequency-domain transform on the combined Doppler spectrogram data c(m) to generate spectrum data C(k);

Step S614: The sign-of-life detection unit 136 determines whether a life is detected according to the spectrum data C(k).

The explanation for Steps S602 to S614 is provided in the preceding paragraphs, and will be omitted here for brevity. The method 600 may generate complex conjugate data according to in-phase components and quadrature components of an echo signal to generate positive velocity energies and negative velocity energies of a target object and detect expansion and contraction movements of a living object, thereby determining whether the target object is a life in an accurate and quick manner.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of detecting a life, the method comprising:
   receiving an echo signal comprising an in-phase component and a quadrature component, the echo signal being generated by a life;
   performing a preprocessing procedure on the echo signal to generate a preprocessed signal;
   generating, according to the preprocessed signal, complex conjugate data associated with the in-phase component and the quadrature component;
   performing a first time-domain-to-frequency-domain transform on the complex conjugate data to generate Doppler spectrogram data comprising a plurality of positive velocity energies and a plurality of negative velocity energies;
   generating combined Doppler spectrogram data according to the plurality of positive velocity energies and the plurality of negative velocity energies;
   performing a second time time-domain-to-frequency-domain transform on the combined Doppler spectrogram data to generate spectrum data; and
   determining whether the life is detected according to the spectrum data.

2. The method claim 1, wherein generating the combined Doppler spectrogram data according to the plurality of positive velocity energies and the plurality of negative velocity energies comprises:
   performing a linear combination of the plurality of positive velocity energies and the plurality of negative velocity energies to generate the combined Doppler spectrum data.

3. The method claim 1, wherein generating the combined Doppler spectrogram data according to the plurality of positive velocity energies and the plurality of negative velocity energies comprises:
   generating the combined Doppler spectrogram data according to an extremum of the plurality of positive velocity energies and the plurality of negative velocity energies at each point in time.

4. The method claim 1, wherein determining whether the life is detected according to the spectrum data comprises:
   when a local extremum of the spectrum data is within a sign-of-life range, determining that the life is detected.

5. The method claim 1, wherein generating the combined Doppler spectrogram data according to the plurality of positive velocity energies and the plurality of negative velocity energies comprises:
   enhancing the plurality of positive velocity energies and the plurality of negative velocity energies in the Doppler spectrogram data to generate a plurality of enhanced positive velocity energies and a plurality of enhanced negative velocity energies; and
   generating the combined Doppler spectrogram data according to the plurality of enhanced positive velocity energies and the plurality of enhanced negative velocity energies.

6. The method claim 1, wherein generating the combined Doppler spectrogram data according to the plurality of positive velocity energies and the plurality of negative velocity energies comprises:
   normalizing the plurality of positive velocity energies and the plurality of negative velocity energies in the Doppler spectrogram data to generate a plurality of normalized positive velocity energies and a plurality of normalized negative velocity energies; and
   generating the combined Doppler spectrogram data according to the plurality of normalized positive velocity energies and the plurality of normalized negative velocity energies.

7. The method claim 1, further comprising:
   filtering out data in the Doppler spectrogram data outside a velocity range.

8. The method claim 1, wherein the preprocessing procedure comprises filtering out a high frequency noise, reducing a sampling frequency, or removing a direct current component.

9. The method claim 1, wherein the first time-domain-to-frequency-domain transform is a short time Fourier transform (STFT).

10. The method claim 1, wherein:
the first time-domain-to-frequency-domain transform is a first Fourier transform, and the second time-domain-to-frequency-domain transform is a second Fourier transform.

11. A detection system for use to detect a life comprising:
a receiver configured to receive an echo signal comprising an in-phase component and a quadrature component, the echo signal being generated by a life;
a preprocessing circuit coupled to the receiver, and configured to perform a preprocessing procedure on the echo signal to generate a preprocessed signal; and
a processor coupled to the preprocessing circuit, and configured to generate, according to the preprocessed signal, complex conjugate data associated with the in-phase component and the quadrature component, perform a first time-domain-to-frequency-domain transform on the complex conjugate data to generate Doppler spectrogram data comprising a plurality of positive velocity energies and a plurality of negative velocity energies, generate combined Doppler spectrogram data according to the plurality of positive velocity energies and the plurality of negative velocity energies, perform a second time time-domain-to-frequency-domain transform on the combined Doppler spectrogram data to generate spectrum data, and determine whether the life is detected according to the spectrum data.

12. The detection system of claim 11, wherein the processor is configured to perform a linear combination of the plurality of positive velocity energies and the plurality of negative velocity energies to generate the combined Doppler spectrum data.

13. The detection system claim 11, wherein the processor is configured to generate the combined Doppler spectrogram data according to an extremum of the plurality of positive velocity energies and the plurality of negative velocity energies at each point in time.

14. The detection system claim 11, wherein the processor is configured to determine that the life is detected when a local extremum of the spectrum data is within a sign-of-life range.

15. The detection system of claim 11, wherein the processor is configured to enhance the plurality of positive velocity energies and the plurality of negative velocity energies in the Doppler spectrogram data to generate a plurality of enhanced positive velocity energies and a plurality of enhanced negative velocity energies, and generate the combined Doppler spectrogram data according to the plurality of enhanced positive velocity energies and the plurality of enhanced negative velocity energies.

16. The detection system of claim 11, wherein the processor is configured to normalize the plurality of positive velocity energies and the plurality of negative velocity energies in the Doppler spectrogram data to generate a plurality of normalized positive velocity energies and a plurality of normalized negative velocity energies, and generate the combined Doppler spectrogram data according to the plurality of normalized positive velocity energies and the plurality of normalized negative velocity energies.

17. The detection system of claim 11, wherein the processor is configured to filter out data in the Doppler spectrogram data outside a velocity range.

18. The detection system of claim 11, wherein the first time-domain-to-frequency-domain transform is a short time Fourier transform.

19. The detection system of claim 11, wherein the first time-domain-to-frequency-domain transform is a first Fourier transform, and the second time-domain-to-frequency-domain transform is a second Fourier transform.

20. The detection system of claim 11, wherein the processor is further configured to filter the combined Doppler spectrogram data to generate filtered Doppler spectrogram data; and
the processor is configured to perform the second time time-domain-to-frequency-domain transform on the filtered Doppler spectrogram data to generate the spectrum data.

* * * * *